United States Patent [19]

Niazi

[11] Patent Number: 4,530,936

[45] Date of Patent: Jul. 23, 1985

[54] COMPOSITION AND METHOD FOR INHIBITING THE ABSORPTION OF NUTRITIONAL ELEMENTS FROM THE UPPER INTESTINAL TRACT

[75] Inventor: Sarfaraz Niazi, Burr Ridge, Ill.

[73] Assignee: Farmacon Research Corporation, Westchester, Ill.

[21] Appl. No.: 512,193

[22] Filed: Jul. 8, 1983

[51] Int. Cl.$^3$ ............................................ A61K 31/025
[52] U.S. Cl. ..................................... 514/749; 514/909
[58] Field of Search ......................................... 424/352

[56] References Cited

U.S. PATENT DOCUMENTS 3,962,439  6/1976  Yokoyama et al. .................. 424/352
4,423,077  12/1983  Slouter ................................. 424/252

FOREIGN PATENT DOCUMENTS 55-72110  5/1980  Japan .................................... 424/352

OTHER PUBLICATIONS

*Perfluoroocytyl Bromide: A Potential Antiobesity Compound*, Journal of Pharmaceutical Sciences, vol. 66, No. 6, p. 907, (Jun. 1977).
*Perfluorodecalin as a Red Cell Substitute from Blood Substitutes and Plasma Expanders*, pp. 69–80, Alan R. Liss, Inc., New York, N.Y., 1978.
*Clinical Studies of a Perfluorochemical Whole Blood Substitute (Fluosol-DA)*, by Misuno et al., pp. 60–69 of vol. Whole Blood Substitute, J. B. Lippincott Company, Ann. Surg., Jan. 1982.

*Primary Examiner*—Douglas W. Robinson
*Attorney, Agent, or Firm*—Leydig, Voit, Osann, Mayer & Holt, Ltd.

[57] ABSTRACT

A method of inhibiting the absorption of nutritional elements, principally food, from the gastrointesinal tract is disclosed which comprises ingesting perfluorodecalin in an amount sufficient to form a nutritional element-impermeable film thereof on at least a substantial part of the inner wall of the upper intestine and maintaining the film for a time long enough to inhibit the absorption from the gastrointestinal tract of a significant proportion of the ingested nutritional elements. An emulsion dosage form is preferred for carrying out this method, which emulsion contains perfluorodecalin, water, and a non-toxic emulsifier, preferably Pluronic F-68, and optionally flavoring and/or coloring agents.

3 Claims, No Drawings

COMPOSITION AND METHOD FOR INHIBITING THE ABSORPTION OF NUTRITIONAL ELEMENTS FROM THE UPPER INTESTINAL TRACT

This invention relates to a new and novel method for inhibiting or preventing the transport of nutritional elements through the wall of the upper intestine and thence into the bloodstream. More particularly, the method provides a very convenient and safe means for inhibiting or preventing the absorption of food elements, and thus the calories contained therein, in at least a substantial portion of the upper intestine, thereby ultimately preventing absorption of nutritional elements and cutting down on the number of calories that the human body will absorb from a given amount of food.

This treatment is important to people who are attempting to restrict their caloric intake, i.e., lose weight, without having to undergo the undesirable psychological impact of dieting. The treatment may also be important to persons who have a need to restrict the absorption of one or more particular nutritional elements, e.g., one who has an allergy to certain proteins and finds it inconvenient to restrict the diet to exclude them. By the practice of this unique method and the use of the composition also described herein, a person can continue to eat essentially a normal meal, but by ingesting the inventive composition shortly before, during, or even shortly after the food intake, the person can coat at least a portion of the upper intestinal wall with a barrier film which prevents transport of the nutritional values through the mucosal wall of the upper intestine and thence into the bloodstream.

BACKGROUND OF THE INVENTION

Prior art workers have attempted to reduce the caloric intake from foods by a host of procedures including, inter alia, appetite suppressants and through the use of starch blockers. The major disadvantages of starch blockers involve pharmacologic reactions, special dietary requirements, serious biological side-effects in some people, and the demonstrated lack of effectiveness of the treatment.

More recently, the use of perfluorooctyl bromide to reduce the caloric intake from foods was suggested in the Journal of Pharmaceutical Sciences, Volume 66, No. 6, page 907 (June 1977). It has now been discovered, however, that perfluorooctyl bromide is contraindicated for inhibiting the absorption of nutritional elements through the upper intestinal tract and that the oral administration of perfluorooctyl bromide may not be entirely safe. Perfluorooctyl bromide is a non-polar molecule having slight electrical charges thereon, from which the bromine atom can be cleaved in the human body. The toxicity of free bromine is well documented. Also perfluorooctyl bromide has two low vapor pressure to be expelled from the intestine in a reasonable time.

Perfluoro compounds have long been known for their chemical stability and their oxygen-carrying capacity. As such, they have been tried and used in clinical studies as substitutes for whole blood or plasma in intravenous injection. In fact, an emulsion of one such perfluoro compound has been subjected to clinical test as reported, for instance, by Dr. Clark in the publication Blood Substitutes and Plasma Expanders, Alan R. Liss, Inc., New York, NY 1978, pp. 69–80. Similar experiments are reported in a number of other publications at about the same time, particularly emanating from work done in Japan at the Kobe National Hospital in Kobe, Japan. The emulsion reported in the aforesaid publications is, however, of no usefulness as an orally ingestible composition for the purpose of coating the intestinal wall. Indeed, the emulsions useful for intravenous injection are contraindicated for the use of this invention since the amount of perfluoro compound is far too small to have any useful effect, and the electolytes employed in the intravenous solution can be cathartic when taken orally in sufficient quantity. Finally, the emulsion proposed for intravenous use is far too costly to ever be used in any useful or practical sense as a calorie inhibitor in a dietary sense.

BRIEF SUMMARY OF THE INVENTION

In view of the contraindications for the use of perfluoro compounds in oral ingestion for the purpose of forming a film barrier on the inner wall of the upper intestine, it was indeed surprising to find that one such perfluoro compound has properties and qualities entirely unique for this indicated purpose. Perfluorodecalin taken either alone in its highly purified form, or in the form of an ingestible emulsion, has the required low surface tension to enable it to coat the wet inner mucosal wall of the upper intestine and to remain in place there for a long enough time to block the absorption of food elements until such elements have been swept through the intestine essentially without absorption. For reasons that will be explained in more detail hereinafter, a useful perfluoro compound must meet a very exacting set of qualifications. It must be highly pure, non-toxic and non-polar, and it must be of a medium volatility such that it will remain in the intestine for a sufficient length of time to be effective and yet has characteristics such that it can be expelled from the intestine in a reasonable time after its usefulness has been exhausted. Finally, it must have a surface tension sufficiently below that of water or aqueous liquids so that it will spread quickly and form an impermeable film or patch on the wet surface of the mucosal wall.

Perfluorodecalin has been available as an article of commerce for more than 2 decades. Details as to its exact structure, methods of purification, purity, and analysis are available in the literature. It can be obtained in highly purified forms by band distillation.

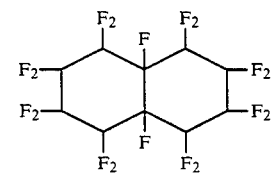

DETAILED DESCRIPTION OF THE INVENTION

Perfluorodecalin is chemically, and biologically inert, due primarily to the strength of the carbon-fluorine bonds and the overall non-polarity of the compound. It is available in highly purified form such that it exhibits no toxicity upon oral administration.

Tests have failed to record any significant absorption of perfluorodecalin into the bloodstream following oral administration, an observation that can be explained by its molecular structure and its aqueous and lipid solubility characteristics.

While perfluorodecalin is available commercially in pure, non-toxic form (greater than 99.9% purity) (Flutec PP5, ISC Chemicals, Ltd., Bristol, England), impure forms of perfluorodecalin may contain low molecular weight perfluoro compounds, branch structures, and incompletely fluorinated compounds, all of which may result in increased toxicity.

The use of perfluorodecalin within the context of the present invention does not result in any chemical interaction with any component of the gastrointestinal tract. Perfluorodecalin does not affect the gastrointestinal mucosa, but rather simply coats the upper intestinal wall.

Digestion of food, therefore, is not affected, but only the physical contact of digested food with the absorption membrane is reduced, thereby reducing or preventing the absorption of nutritional values such as carbohydrates, fats and proteins through the gastrointestinal tract. In this regard, it should be noted that the absorption barrier is indiscriminate and results in the reduced uptake of all nutritional values as well as vitamins and minerals.

Due to the low surface tension (about 25 dynes/cm) of perfluorodecalin, after ingestion thereof the compound easily and quickly spreads over aqueous membranes so as to coat the upper gastrointestinal tract. Although the extent of the coating of the gastrointestinal tract varies with the amount of perfluorodecalin ingested, generally a normal or effective dose of perfluorodecalin will not coat the entire gastrointestinal tract, but rather merely patches or portions thereof. The area and position of a given patch of the barrier film coating may change dynamically throughout the period that absorption of food would normally take place. Thus, the user achieves a reduction of caloric intake, but normally absorbs enough nutritional values to avoid symptoms of malnutrition. In one sense this method and composition achieves the effect of a temporary shortening of the upper intestine without lasting ill-effects.

The perfluorodecalin coating of the gastrointestinal tract is not permanent in nature, but rather is of limited duration. In time, the perfluorodecalin is entirely eliminated from the body of the person who has ingested it. The duration of the perfluorodecalin coating and, thus, the effectiveness of the herein described method of reducing the intake of nutritional values depends on such factors as the dosage amount, the gastrointestinal motility, the type of food consumed (which, in turn, affects motility), and the general nutritional status of the patient. In general, a typical dosage of at least about 5 ml, taken within a reasonable time before, with or just after the ingestion of food will remain effective in the body for a time sufficient to alter the absorption characteristics of the intestine.

I have found that the inhibition of the absorption of nutritional elements through the gastrointestinal wall in a particular individual can be directly controlled by varying the dosage amount of perfluorodecalin ingested, and can also be influenced by varying the timing of dosages. For example, two 5 ml doses of perfluorodecalin spaced one hour apart just before ordering a meal is more effective in inhibiting the absorption of nutritional elements than a single 10 ml dose. Body weight of a person is of relatively minor significance.

The following Tables I and II establish the effectiveness of the method and composition of this invention in causing weight loss in animals.

TABLE 1

SUMMARY OF BODY WEIGHT (GMS.) DATA FROM 21-DAY DIET STUDY IN RATS
(Diet mixed with perfluorodecalin, 7%)

| Group | Day 0 | Day 7 | Day 14 | Day 21 | Total Change |
|---|---|---|---|---|---|
| Control, Male | 150.9 | 198.3 | 252.0 | 297.1 | 146.2 |
| Treatment, Male | 151.0 | 179.7* | 226.0* | 268.7* | 117.8** |
| Control, Female | 115.8 | 137.4 | 160.0 | 179.1 | 63.3 |
| Treatment, Female | 115.6 | 126.9* | 148.4* | 162.8* | 47.3** |

\* = statistically significant at 95% confidence internal
\*\* = statistically significant at 99% confidence internal

TABLE II

SUMMARY OF BODY WEIGHT PERCENT CHANGE FROM 21-DAY ORAL INTUBATION STUDY IN RATS (1 ml of perfluorodecalin prior to intubation and 1 ml administered 30 min. after the first dose)

| Group | Day 0 | Day 7 | Day 14 | Day 21 |
|---|---|---|---|---|
| Control, Male | 0 | 3 | 7 | 10 |
| Treatment, Male | 0 | 1 | 2.5 | 4** |

\*\*significantly different at 99% confidence internal

While the ingestion of pure perfluorodecalin alone is quite effective in inhibiting the transport of nutritional elements through the wall of the gastrointestinal tract, the ingestion of perfluorodecalin when combined with dry or wet foods is equally effective. Thus it can be mixed with cereals, vegetables, bread and the like. It is perhaps not surprising in view of its complete chemical inertness and stability, that perfluorodecalin has no taste at all.

The perfluorodecalin can also be made into an aqueous or aqueous-alcoholic emulsion to which may be added flavor and/or coloring agents. The perfluorodecalin emulsion may be obtained through the use of any suitable non-toxic emulsifier such as the Pluronics (addition products of ethylene oxide and polypropylene glycols). The emulsifier Pluronic F-68 (available from BASF and Wyandotte Corporation) is especially useful as an emulsifying agent in the preparation of a perfluorodecalin emulsion due to its well-documented lack of toxicity (Pluronic F-68 has been approved for use in humans by the U.S. Food and Drug Administration), its value as a general emulsifier, ready availability, and ability to form stable, fine-particle emulsions with perfluorodecalin.

The following is an exemplary but not limiting formulation useful in the practice of this invention.

| EMULSION COMPOSITION CONTAINING PERFLUORODECALIN | |
|---|---|
| Perfluorodecalin | 70.0% w/v |
| Pluronic F-68 | 4.7% w/v |
| Phospholipids, eggyolk | 0.4% w/v |
| Flavor, various | qs. w/v |
| Color, food grade | qs. w/v |
| Sweetner, sodium saccharin or aspartame | qs. w/v |
| Water | qs. to 100 |

Procedure: Of the several possible methods, one can mix the surfactant (Pluronic F-68) with water in a Hobart mixer and slowly pour perfluorodecalin in the mixer, pass the mixture through a homogenizer, either ultrasonic or mechanical. Add phospholipids and once again pass the mixture through the homogenizer. Finally, add the remaining components and mix in the mixer.

While the stabilityy of a perfluorodecalin emulsion is not critical to its effectiveness in inhibiting the transport of nutritional elements through the wall of the gastrointestinal tract (since, as stated above, perfluorodecalin alone is effective in this regard), nor is the particle size, the advantages of an esthetic, stable emulsion of small particle size are easily apparent.

Although other perfluorocarbons are generally inert, their effective use in the context of the present invention is not possible for several reasons. In general, straight-chain perfluoroalkanes such as perfluorooctane and perfluorohexane are not suitable for use in the present invention because the manufacture of the shorter-chain perfluoroalkanes results in formation of side products which are quite difficult and costly to remove. Yet, impure perfluoroalkanes are too toxic for oral use. Furthermore, the shorter-chain perfluoroalkanes are too volatile (have too high vapor pressure) as to cause rapid evaporation of such within the body thereby causing the compound to leave the gastrointestinal tract too rapidly to be effective as a barrier film. Long-chain perfluoroalkanes lack the necessary surface tension lowering quality to provide a rapidly spreading barrier film, or are too slowly excreted due to low volatility.

If a bromine atom is present with the alkane in a perfluoroalkane, such as is the case with perfluorooctyl bromide, then the compound becomes slightly polar such that bromine can be cleaved from the remainder of the molecule within the human body. In general, a carbon-bromine bond is not as strong as a carbon-fluorine bond so the hydrolysis of a compound containing a carbon-bromine bond in human bodily fluids is much more likely to result.

The cyclic perfluoroalkanes are non-polar, stable and effective surface tension lowering agents. But while perfluorocyclohexane is in a chemical sense similar to perfluorodecalin, the use of perfluorocyclohexane in the context of the present invention is ineffective due to its high vapor pressure. Perfluorocyclohexane is too rapidly excreted and thus remains in the body for too short a period of time to be effective as a barrier film.

I claim:

1. The method of inhibiting or preventing the absorption of at least one nutritional elements selected from the group consisting of carbohydrates, fats, proteins, vitamins, and minerals from the gastrointestinal tract which comprises ingesting perflorodecalin in an amount sufficient to form a nutritional element-impermeable film thereof on at least a substantial part of the inner wall of the upper intestine and maintaining said film for a time long enough to inhibit absorption of nutritional elements from the gastrointestinal tract.

2. The method claimed in claim 1, wherein the amount of perfluorodecalin ingested is at least 5 milliliter.

3. The method as claimed in claim 1, wherein the ingestion of perfluorodecalin occurs shortly before, during or shortly after the ingestion of nutritional elements.

* * * * *